United States Patent [19]

Shimano et al.

[11] Patent Number: 4,561,880
[45] Date of Patent: Dec. 31, 1985

[54] 1H[1,2,4]-TRIAZOLO[1,2-A]PYRIDAZINE-1,3-DIONES USEFUL AS HERBICIDES

[75] Inventors: Shizuo Shimano, Ageo; Shinichi Kobayashi, Fuchu; Mikio Yanagi, Okegawa; Osamu Yamada, Ageo; Atsuhiko Shida, Koga; Fumio Futatsuya, Ohmiya, all of Japan

[73] Assignee: Nippon Kayaku Kabushiki Kaisha, Tokyo, Japan

[21] Appl. No.: 523,585

[22] Filed: Aug. 16, 1983

[30] Foreign Application Priority Data

Sep. 2, 1982 [JP] Japan .................. 57-151696
Sep. 13, 1982 [JP] Japan .................. 57-158227

[51] Int. Cl.$^4$ .............. A01N 43/56; A01N 43/58; A01N 43/62; C07D 487/04; C07D 231/04; C07D 237/04; C07D 243/02
[52] U.S. Cl. ...................... 71/92; 544/236; 544/224; 548/264; 548/356; 260/245.5; 260/239 BC
[58] Field of Search .............. 544/236; 548/264; 260/245.5; 71/92

[56] References Cited

U.S. PATENT DOCUMENTS 4,249,934  2/1981  Wakabayashi et al. .......... 71/92
4,439,229  3/1984  Swithenbank ................ 548/513

FOREIGN PATENT DOCUMENTS 2071100  9/1981  United Kingdom ............ 548/513

OTHER PUBLICATIONS

Ohta et al, Chem. Abstracts, vol. 85:42085s (1976).

Wakabayashi et al, Chem. Abstracts, vol. 91:169807h (1979).

Primary Examiner—Donald G. Daus
Assistant Examiner—William A. Teoli, Jr.
Attorney, Agent, or Firm—Henry C. Nields

[57] ABSTRACT

A compound of the formula:

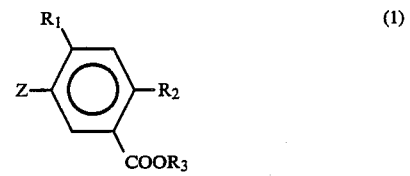

wherein Z is

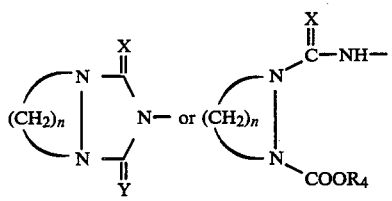

wherein $R_4$ is lower alkyl, X and Y are oxygen or sulfur and n is an integer of 3 to 6, $R_1$ is hydrogen or halogen, $R_2$ is halogen and $R_3$ is hydrogen or $C_1$–$C_8$-alkyl which may have lower alkoxy; a herbicidal composition containing said compound as an effective component; a method for killing weeds using said compound; and processes for the production of said compound, are disclosed hereinafter.

3 Claims, No Drawings

1H[1,2,4]-TRIAZOLO[1,2-A]PYRIDAZINE-1,3-DIONES USEFUL AS HERBICIDES

DETAILED DESCRIPTION OF THE INVENTION

This invention relates to a compound of the formula:

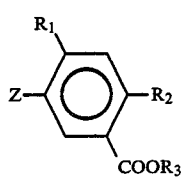

(1)

wherein Z is

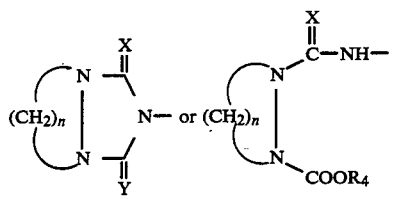

wherein $R_4$ is lower alkyl, X and Y are oxygen or sulfur and n is an integer of 3 to 6; $R_1$ is hydrogen or halogen, $R_2$ is halogen and $R_3$ is hydrogen or $C_1$-$C_8$-alkyl which may have lower alkoxy; a herbicidal composition containing said compound as an effective component; a method for killing weeds using said compound; and processes for the production of said compound.

It is known that, among the compounds similar to the compound of the present invention, there are compounds having herbicidal activity (Japanese Patent Kokai Nos. 50-160429, 51-35435, 52-83687, 53-44587, 51-38425, 52-83552 and 53-40785).

The present inventors have found that the compound of the formula (1) has very high herbicidal activity. Furthermore, the present inventors have found that the compounds of the formula (1) have very low phytotoxicity against crops and, therefore, they become practical herbicide.

The compound of the formula (1) exhibits excellent herbicidal effect in a paddy field at a low dosage not only against annual weeds such as barnyard grasses and broadleaf weeds, but also against perennial weeds such as mizugayatsuri, bulrush, water chestnut, needle spikerush and arrowhead. The compounds of the formula (1) also show a good herbicidal effect by both pre- and post-emergence treatments in an up-land, especially against broadleaf weeds as those of amaranth, goosefoot and buckwheat families at a low dosage.

Furthermore, the compound of the formula (1) is hardly phytotoxic to crops such as rice, wheat, oat, corn, soybean, cotton and sunflower.

The compound of the formula (1) of the present invention can be produced by the processes described in (A), (B), (C), (D) and (E) below.

(A):

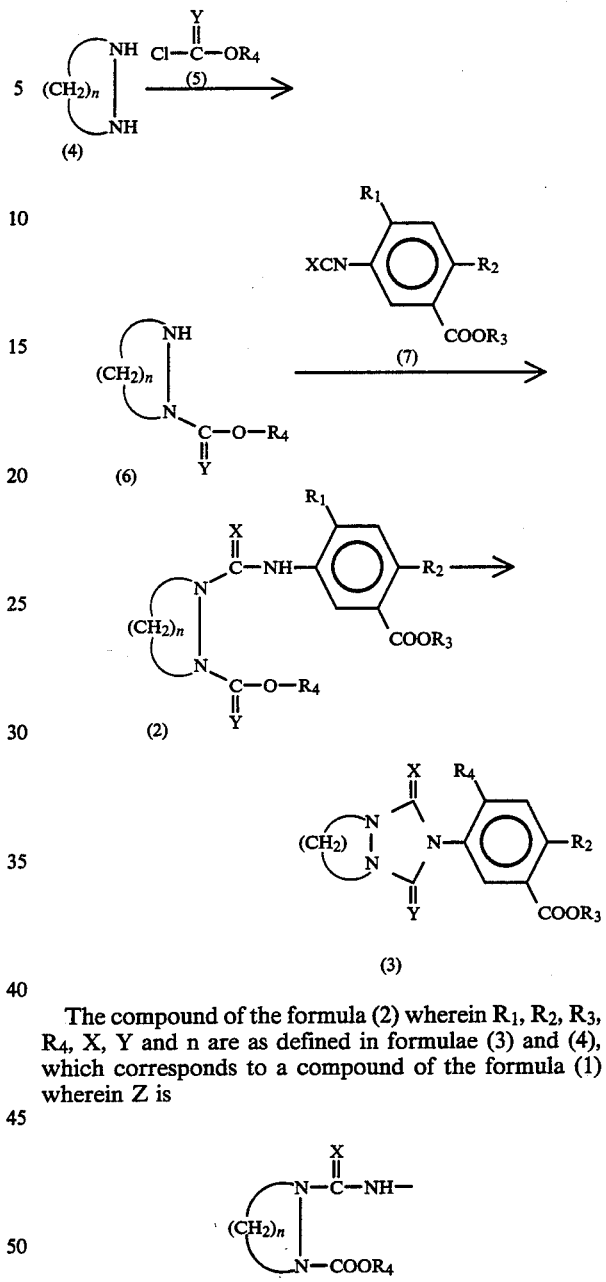

The compound of the formula (2) wherein $R_1$, $R_2$, $R_3$, $R_4$, X, Y and n are as defined in formulae (3) and (4), which corresponds to a compound of the formula (1) wherein Z is can be obtained as follows:

A compound of the formula (4) (for example, $N^1,N^2$-trimethylene hydrazine, $N^1,N^2$-hexamethylene hydrazine) can be reacted with a chlorocarbonic ester derivative of the formula (5) wherein $R_4$ is lower alkyl, Y is oxygen or sulfur in an organic solvent such as alcohols (methanol, ethanol) and the inert solvent defined after, at 0°–50° C., preferably at 10°–20° C. to produce an $N^1,N^2$-alkylene-$N^1$-alkoxycarbonylhydrazine derivative of the formula (6) wherein $R_4$, Y are as defined in the formula (5), n is as defined in the formula (3), and the compound of the formula (6) can be reacted with a substituted phenylisocyanate or a substituted phenylthioisocyanate derivative of the formula (7) wherein $R_1$, $R_2$, $R_3$ and X are as defined in the formula (3) preferably in an inert solvent, at 0°–100° C. more preferably at 5°–50° C. for 20 min. to 3 hrs. to produce a compound of the formula (2).

(B):

The compound of the formula (3) wherein $R_1$, $R_2$, $R_3$, X, Y and n are as defined above, which corresponds to the compound of the formula (1) wherein Z is

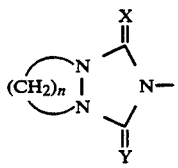

can be obtained by cyclizing the compound of the formula (2) by heating preferably under reflux in the presence of a base at 60°–150° C. preferably at 80°–120° C. for 30 min. to 8 hrs.

(C):

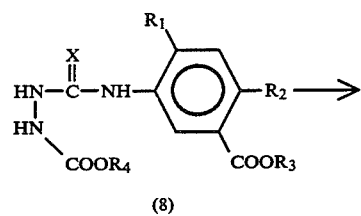

(8)

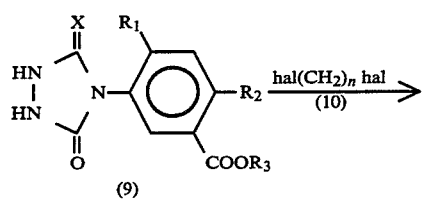

(9)

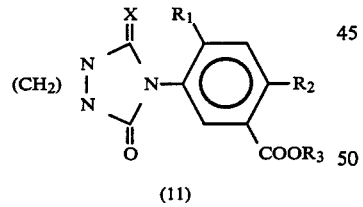

(11)

The compound of the formula (11) wherein $R_1$, $R_2$, $R_3$, X and n are as defined in the formula (1), which corresponds to the compound of the formula (1) wherein Z is

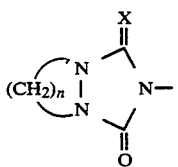

can be produced preferably by reacting a sodium salt

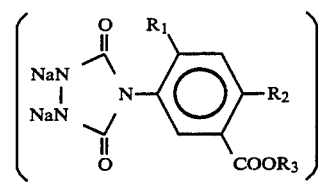

of the compound of the formula (9) with a compound of the formula (10) preferably at 120°–150° C. in an inert solvent.

The compound of the formula (9) can be produced by cyclizing a compound of the formula (8) by heating, preferably under reflux, at 60°–150° C., preferably at 80°–120° C. in the presence of a base in an inert solvent.

The compound of the formula (8) is obtained by reacting an N-alkoxycarbonylhydrazine with the compound of the formula (7), preferably in an inert solvent, at −10°–100° C., more preferably at −5°–50° C.

(D):

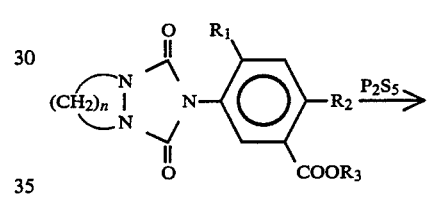

(12)

(13)

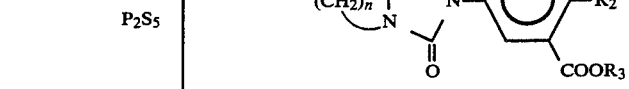
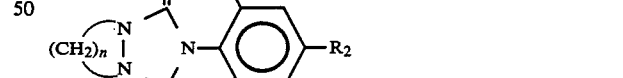
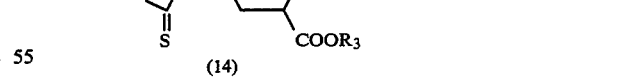
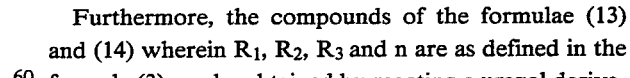

(14)

Furthermore, the compounds of the formulae (13) and (14) wherein $R_1$, $R_2$, $R_3$ and n are as defined in the formula (3) can be obtained by reacting a urazol derivative of the formula (12) with a phosphorus polysulfide such as $P_2S_5$ under heating in an organic solvent such as benzene, toluene, xylene, preferably at 80°–140° C., or reacting said urazol derivative with preferably $B_2S_3$ or $SiS_2$ in chloroform under reflux.

(E):

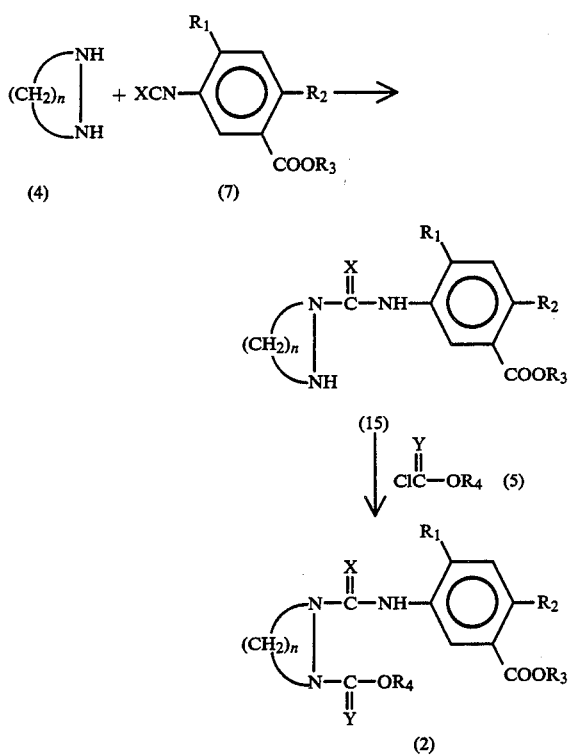

The former compound of the formula (2) also can be obtained by reacting the compound of the formula (4) with the compound of the formula (7) in an inert solvent preferably at −10°–30° C. to produce a compound of the formula (15) wherein $R_1$, $R_2$, $R_3$, X and n are as defined in the formula (3), and then reacting thus obtained compound with a compound of the formula (5) in an inert solvent at 0°–50° C.

The compounds of the formulae (4) and (6) which are starting materials of the compound of the formula (1) can be obtained by the known method (Japanese Patent Kokai No. 51-65757).

The compound of the formula (7) can be obtained by reacting a substituted aniline derivative of the formula (16) wherein $R_1$, $R_2$, $R_3$ are as defined in the formula (3) with phosgene or thiophosgene of the formula (17) or ClCOOCCl₃.

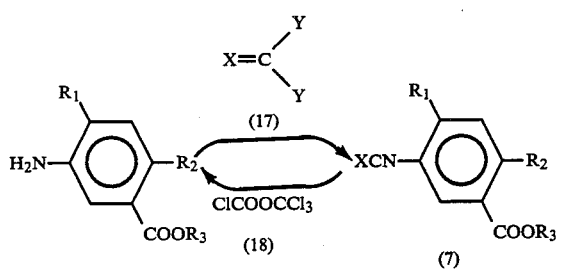

The above reaction can be conducted in the absence of a solvent, but preferably it is conducted in an inert solvent, generally at −20° C.—boiling point of the solvent, preferably at 0° C.–120° C.

The reaction is conducted preferably under atmospheric pressure, but it can be conducted under pressure or reduced pressure.

As examples of the bases used in the present invention, there can be mentioned alkali metal salts such as sodium hydroxide or potassium hydroxide; alkaline earth metal salts such as calcium hydroxide or magnesium hydroxide and barium hydroxide; alcoholates of alkali metal such as sodium alcoholates or potassium alcoholates; trialkylamines; pyridine; picoline, and usually the bases can be used in catalytic amount.

As examples of the inert solvents, there can be mentioned aromatic hydrocarbons such as benzene, toluene, xylenes, chlorobenzenes; aliphatic hydrocarbons such as n-hexane, n-heptane or petroleum ether; alicyclic hydrocarbon such as cyclohexane; halogenated hydrocarbons such as chloroform, carbontetrachloride or perchloroethylene; ketones such as acetone or methylethylketone; ethers such as ethylether, tetrahydrofuran or dioxane; alcohols such as methanol or ethanol; esters such as ethylacetate or butylacetate; amides such as N,N-dimethylformamide or N,N-diethylformamide; or water.

In the formula (1), as examples of halogens there can be mentioned chloro, bromo or fluoro. As examples of lower alkoxys there can be mentioned methoxy or ethoxy.

As examples of $C_1$-$C_8$-alkyls, there can be mentioned methyl, ethyl, n-propyl, iso-propyl, n-butyl, s-butyl, iso-butyl, tert-butyl, n-pentyl, n-hexyl, n-heptyl, n-octyl, 2-ethylhexyl or 1,3-dimentylbutyl.

In the formula (4), as examples of lower alkyls of $R_4$, there can be mentioned $C_1$-$C_4$ alkyls such as methyl, ethyl, n-propyl, iso-propyl, n-butyl or sec-butyl.

As preferable compounds in the present invention, there can be mentioned those of the formula (1) wherein
(a) Z is

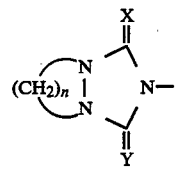

(n is 3 or 4, X and Y are oxygen or sulfur), $R_1$ is chloro or fluoro, $R_2$ is chloro or bromo, $R_3$ is $C_2$-$C_4$-alkyl, (b) Z is

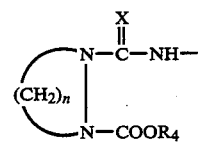

(n is 3 or 4, $R_4$ is $C_2$-$C_4$-alkyl and X and Y are oxygen or sulfur), $R_1$ is chloro of fluoro, $R_2$ is chloro or bromo and $R_3$ is $C_2$-$C_4$-alkyl.

As most preferable compounds in the present invention, there can be mentioned

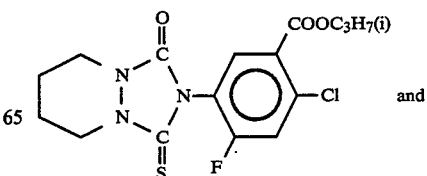

and

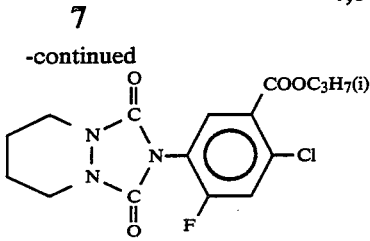

The present invention will be illustrated in the following examples.

SYNTHESIS EXAMPLE 1

1,2-trimethylene-4-(2-fluoro-4-chloro-5-ethoxycarbonylphenyl)urazol (Compound No. 1).

1.44 g (0.01 mol) of 1,2-trimethylenehydrazine-1-carboxylic acid ethylester were dissolved in 30 ml of toluene and 2.3 g (0.01 mol) of 2-fluoro-4-chloro-5-ethoxycarbonylphenylisocyanate were added to the solution, and after the mixture were stirred for 1 hr. at room temperature, 2 ml of N,N-dimethylformamide and 0.3 g of sodium hydroxide were added thereto and the whole was stirred for 15 min. at 100°–110° C. After cooling, the reaction mixture was washed with water, dried over anhydrous $Na_2SO_4$ and concentrated to obtain crystals. Upon recrystallization from ethanol, 1.21 g of pale brown crystals were obtained.

Yield: 37.2%, M.p.: 156°–158° C.

Elementary analysis: $C_{14}H_{18}FClN_3O_4$; calculated: C: 49.20, H: 3.83, N: 12.29; found: C: 49.50, H: 3.88, N: 12.32.

SYNTHESIS EXAMPLE 2

1,2-tetramethylene-4-(2-fluoro-4-bromo-5-isopropoxycarbonylphenyl)urazol (Compound No. 13).

1.6 g (0.01 mol) of 1,2-tetramethylenehydrazine-1-carboxylic acid ethylester were dissolved in 30 ml of toluene and 3 g (0.01 mol) of 2-fluoro-4-bromo-5-isopropoxycarbonylphenylisocyanate were added to the solution, and after the mixture was stirred for 1 hr. at room temperature, 2 ml of N,N-dimethylformamide and 0.3 g of sodium hydroxide were added thereto and the whole was heated at 80° C. for 30 min. After cooling, the reaction mixture was washed with water, dried over anhydrous $Na_2SO_4$ and concentrated to obtain crystals. Upon recrystallization from toluene, 27.1 g of white crystals were obtained. Yield: 65%, M.P.: 161°–162° C.

Elementary analysis: $C_{16}H_{17}FBrN_3O_4$; Calculated: C: 46.39, H: 4.13, N: 10.14; Found: C: 46.68, H: 4.14, N: 10.30.

SYNTHESIS EXAMPLE 3

1,2-tetramethylene-4-(4-chloro-3-methoxycarbonylphenyl)thiourazol (Compound No. 14).

1.6 g (0.1 mol) of 1,2-tetramethylenehydrazine-1-carboxylic acid ethylester were dissolved in 40 ml of xylene and when 2.2 g (0.01 mol) of 4-chloro-3-methoxycarbonylphenylisothiocyanate were added to the solution, white crystals were precipitated. After precipitating, the mixture was stirred at room temperature for 1 hr., 200 mg of hydrous $Na_2SO_4$ were added thereto and the whole was heated under reflux for 3 hrs. After cooling, the reaction mixture was washed with water, dried over anhydrous $Na_2SO_4$ and concentrated to obtain crystals. Upon recrystallization from the mixture of n-hexane and toluene, 2.2 g of pale yellow crystals were obtained.

Yield: 64%, M.P.: 126°–128° C.

Elementary analysis: $C_{14}H_{14}ClN_3O_3S$; Calculated: C: 49.48, H: 4.15, N: 12.36; Found: C: 49.41, H: 4.19, N: 12.08.

SYNTHESIS EXAMPLE 4

1,2-tetramethylene-4-(4-chloro-3-isopropoxycarbonylphenyl)dithiourazol (Compound No. 19).

3.6 g of (0.01 mol) 1,2-tetramethylene-4-(4-chloro-3-isopropoxycarbonylphenyl)thiourazol and 2.2 g (0.01 mol) of diphosphorus pentasulfide were added to 60 ml of xylene and heated under stirring at 100°–110° C. for 9 hrs.

After cooling, the produced precipitates were removed by filtration and the filtrate was washed with water, dried over anhydrous $Na_2SO_4$ and then the oil was obtained by concentration. Thus obtained oil was purified by the column chromatography (silica gel) to obtain 1.75 g of yellow crystals.

Yield: 40%, M.p.: 161°–163° C.

Elementary analysis: $C_{16}H_{18}ClN_3O_2S_2$; Calculated: C: 50.05, H: 4.72, N: 10.94; Found: C: 50.21, H: 4.77, N: 10.69.

SYNTHESIS EXAMPLE 5

1,2-tetramethylene-4-(2-fluoro-4-chloro-5-sec-butoxycarbonylphenyl)thiourazol (Compound No. 26).

8.3 g (0.0175 mol) of 1,2-tetramethylene-1-carboisobutoxy-2-(fluoro-4-chloro-5-sec-butoxycarbonyl phenylthiocarbamoyl)hydrazine were dissolved in 100 ml of toluene, 3 ml of N,N-dimethylformamide and 0.5 g of sodium hydroxide were added to the solution and the mixture was heated at 100°–110° C. for 30 min. After cooling, the reaction mixture was washed with water, dried over anhydrous $Na_2SO_4$, and concentrated to obtain crystals. Upon recrystallization from the mixture of n-hexane and toluene, 5 g of white crystals were obtained. Yield: 71.4%, M.p.: 131.5°–132.5° C.

Elementary analysis: $C_{17}H_{19}FClN_3O_3S$; Calculated: C: 51.06, H: 4.78, N: 10.50; Found: C: 51.29, H: 4.82, N: 10.45.

SYNTHESIS EXAMPLE 6

1,2-pentamethylene-4-(2-fluoro-4-chloro-5-isopropoxycarbonylphenyl)urazol (Compound No. 30).

2.9 g (0.0067 mol) of 1,2-pentamethylene-1-carboethoxy-2-(2-fluoro-4-chloro-5-isopropoxycarbonylphenylcarbamoyl)hydrazine were dissolved in 70 ml of toluene, 2 ml of N,N-dimethylformamide and 0.3 g of sodium hydroxide were added to the solution and the mixture was heated under reflux for 30 min. After cooling, the reaction mixture was washed with water, dried over anhydrous $Na_2SO_4$ and concentrated to obtain crystals. Upon recrystallization from the mixture of n-hexane and toluene, 2.5 g of white crystals were obtained. Yield: 97.2%, M.p.: 105.5°–106° C.

Elementary analysis: $C_{17}H_{19}FClN_3O_4$; Calculated: C: 53.20, H: 4.98, N: 10.94; Found: C: 53.43, H: 4.95, N: 11.18.

SYNTHESIS EXAMPLE 7

1,2-pentamethylene-4-(4-bromo-3-isopropoxycarbonylphenyl)thiourazol (Compound No. 33).

1.5 g (0.087 mol) of 1,2-pentamethylenehydrazine-1-carboxylic acid ethylester were dissolved into 40 ml of xylene, 2.6 g (0.0087 mol) of 4-bromo-3-isopropoxycarbonylphenylisothiocyanate were added to the solution and the mixture was stirred for 1 hr., 300 mg of anhydrous Na₂SO₄ were added to the mixture and then the whole was heated under reflux for 12 hrs. After cooling, the reaction mixture was washed with water, dried over anhydrous Na₂SO₄ and concentrated to obtain the oil. Thus obtained oil was purified by the column chromatography (cilica gel) to obtain 1.5 g of yellow oil. Yield: 40.2%, reflectance: $n_D^{25}$ 1.5959.

Elementary analysis: $C_{17}H_{20}BrN_3O_3S$; Calculated: C: 47.89, H: 4.72, N: 9.85; Found: C: 48.15, H: 4.69, N: 9.92.

The following compounds were obtained by the above processes.

2-fluoro-4-chloro-5-ethoxycarbonylphenylisocyanate were added to the solution and the whole was stirred at room temperature for 1 hr. The reaction mixture was washed with water, dried over anhydrous Na₂SO₄ and concentrated to obtain the crystal. The crystals were purified by column chromatography (silica gel, developing solvent:hexane:ethylacetate) to produce 4.29 g of white crystals, Yield: 65%, M.p.: 82°–83° C.

Elementary analysis: $C_{16}H_{19}FClN_3O_5$; Calculated: C: 49.55, H: 4.93, N: 10.83; Found: C: 49.75, H: 4.94, N: 10.91.

TABLE 1

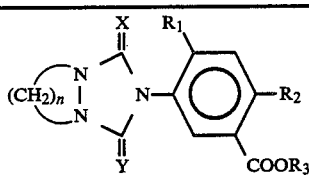

| Compound No. | n | X | Y | R₁ | R₂ | R₃ | M.p. (°C.) or refractive index | Appearance |
|---|---|---|---|---|---|---|---|---|
| 1 | 3 | O | O | F | Cl | C₂H₅ | 156–158 | pale brown crystal |
| 2 | 3 | O | S | F | Cl | C₂H₅ | amorphous | " |
| 3 | 3 | O | S | Cl | Cl | C₂H₅ | 132–134 | pale yellow crystal |
| 4 | 3 | O | S | H | Cl | C₃H₇(i) | 169–171 | " |
| 5 | 3 | O | S | F | Cl | C₃H₇(i) | 178–180 | pale brown crystal |
| 6 | 3 | O | S | H | Br | C₄H₉(sec) | 111–113 | pale yellow crystal |
| 7 | 4 | O | O | F | Cl | CH₃ | 131–133 | white crystal |
| 8 | 4 | O | O | F | Cl | C₂H₅ | 121–123 | " |
| 9 | 4 | O | O | H | Cl | C₃H₇(i) | 100–100.5 | " |
| 10 | 4 | O | O | H | Br | C₃H₇(i) | 128.5–130 | " |
| 11 | 4 | O | O | Cl | Cl | C₃H₇(i) | 140–142 | " |
| 12 | 4 | O | O | F | Cl | C₃H₇(i) | 147–148 | " |
| 13 | 4 | O | O | F | Br | C₃H₇(i) | 161–162 | " |
| 14 | 4 | O | S | H | Cl | CH₃ | 126–128 | pale yellow crystal |
| 15 | 4 | O | S | H | Br | C₂H₅ | 105–107 | yellow crystal |
| 16 | 4 | O | S | H | Cl | C₂H₅ | 104–106 | pale brown crystal |
| 17 | 4 | O | S | H | Cl | C₃H₇(n) | 72–74 | yellow crystal |
| 18 | 4 | O | S | H | Cl | C₃H₇(i) | 120–127 | pale yellow crystal |
| 19 | 4 | S | S | H | Cl | C₃H₇(i) | 161–163 | yellow crystal |
| 20 | 4 | O | S | H | Br | C₃H₇(i) | 133.5–135.5 | white crystal |
| 21 | 4 | O | S | Cl | Cl | C₂H₅ | 134–135.5 | " |
| 22 | 4 | O | S | F | Cl | CH₃ | 188–190 | " |
| 23 | 4 | O | S | F | Cl | C₂H₅ | 130–132 | pale yellow crystal |
| 24 | 4 | O | S | F | Cl | C₃H₇(i) | 132–133.5 | white crystal |
| 25 | 4 | O | S | F | Br | C₃H₇(i) | 147–148.5 | pale brown crystal |
| 26 | 4 | O | S | F | Cl | C₄H₉(sec) | 131.5–132.5 | white crystal |
| 27 | 4 | O | S | H | Cl | C₄H₉(sec) | 88–90 | pale brown crystal |
| 28 | 4 | O | S | H | Br | C₄H₉(sec) | 88–90 | pale yellow crystal |
| 29 | 5 | O | O | H | Br | C₃H₇(i) | 111–112 | white crystal |
| 30 | 5 | O | O | F | Cl | C₃H₇(i) | 105.5–106 | " |
| 31 | 5 | O | S | H | Cl | CH₃ | 155–158 | pale yellow crystal |
| 32 | 5 | O | S | H | Cl | C₃H₇(i) | $n_D^{25}$1.5762 | yellow oil |
| 33 | 5 | O | S | H | Br | C₃H₇(i) | $n_D^{25}$1.5959 | " |
| 34 | 5 | O | S | F | Cl | C₃H₇(i) | 142–143.5 | white crystal |
| 35 | 5 | O | S | F | Br | C₃H₇(i) | 171–173 | brown crystal |
| 36 | 4 | O | S | F | Cl | —CH(CH₃)—CH₂—CH(CH₃)—CH₃ | $n_D^{25}$1.5620 | pale yellow oil |
| 37 | 4 | O | S | F | Cl | CH₂CH₂OCH₃ | 83–85 | white crystal |
| 38 | 4 | O | S | F | Cl | CH₂—CH(CH₂CH₃)(CH₂)₃CH₃ | $n_D^{25}$1.5551 | pale yellow oil |

SYNTHESIS EXAMPLE 8

1,2-trimethylene-1-ethoxycarbonyl-2-(2-fluoro-4-chloro-5-ethoxycarbonylphenylcarbamoyl)hydrazine (Compound No. 40).

2.46 g (0.017 mol) of 1,2-trimethylenehydrazine were dissolved in 30 ml of toluene and 4.14 g (0.017 mol) of Even if 1,2-trimethylenehydrazine-1-carboxylic acid hydrochloride was used instead of 1,2-trimethylenehydrazine-1-carboxylic acid, the above compound (Compound No. 40) was obtained by using triethylamine.

SYNTHESIS EXAMPLE 9

1,2-trimethylene-1-carboethoxy-2-(4-bromo-3-sec-butoxycarbonylphenylthiocarbamoyl)hydrazine (Compound No. 45).

1.44 g (0.01 mol) of 1,2-trimethylenehydrazine-1-carboxylic acid ethylester were dissolved in 30 ml of benzene and 3.1 g (0.01 mol) of 4-bromo-3-sec-butoxycarbonylphenylisothiocyanate were added to the solution and the mixture was stirred for 1 hr. at room temperature. The reaction mixture was concentrated to obtain the crystals. Upon recrystallization from the mixture of hexane and toluene, 3.9 g of white crystals were obtained. Yield: 85%, M.p.: 119°–120.5° C.

Elementary analysis: $C_{18}H_{24}BrN_3O_4S$; Calculated: C: 47.16, H: 5.27, N: 9.16; Found: C: 47.08, H: 5.53, N: 9.26.

The following compounds were obtained by the above processes.

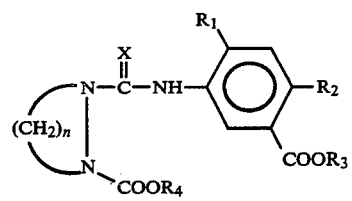

TABLE 2

| Compound No. | n | X | $R_1$ | $R_2$ | $R_3$ | $R_4$ | M.p. (°C.) or refractive index | Appearance |
|---|---|---|---|---|---|---|---|---|
| 39 | 3 | O | F | Cl | $CH_3$ | $C_2H_5$ | 103–105 | white crystal |
| 40 | 3 | O | F | Cl | $C_2H_5$ | " | 82–83 | " |
| 41 | 3 | O | F | Cl | $C_3H_7(i)$ | " | 102–105 | " |
| 42 | 3 | S | H | Cl | $CH_3$ | " | 127–128 | pale yellow crystal |
| 43 | 3 | S | H | Cl | $C_3H_7(i)$ | " | 108–109 | " |
| 44 | 3 | S | F | Cl | $C_3H_7(i)$ | " | 87–88.5 | pale brown crystal |
| 45 | 3 | S | H | Br | $C_4H_9(sec)$ | " | 119–120.5 | white crystal |
| 46 | 3 | S | Cl | Cl | $C_2H_5$ | " | 102–104 | " |
| 47 | 3 | S | F | Cl | $C_2H_5$ | " | 97–98.5 | pale brown crystal |
| 48 | 4 | O | H | Cl | $C_3H_7(i)$ | " | 119–122 | " |
| 49 | 4 | O | F | Cl | $CH_3$ | " | 126.5–127 | white crystal |
| 50 | 4 | O | F | Cl | $C_2H_5$ | " | 87–88 | " |
| 51 | 4 | O | F | Cl | $C_3H_7(i)$ | " | $n_D^{25}1.5249$ | yellow oil |
| 52 | 4 | O | H | Br | $C_3H_7(i)$ | " | 125–126 | white crystal |
| 53 | 4 | O | Cl | Cl | $C_3H_7(i)$ | " | 69–71 | " |
| 54 | 4 | O | F | Br | $C_3H_7(i)$ | " | 74–75 | " |
| 55 | 4 | O | F | Cl | $C_3H_7(i)$ | $C_4H_9(i)$ | $n_D^{25}1.5161$ | pale yellow oil |
| 56 | 4 | O | F | Br | $C_3H_7(i)$ | " | $n_D^{25}1.5216$ | " |
| 57 | 4 | S | H | Cl | $CH_3$ | $CH_3$ | 181.5–183.5 | pale yellow crystal |
| 58 | 4 | S | H | Cl | $CH_3$ | $C_2H_5$ | 144–146 | white crystal |
| 59 | 4 | S | H | Cl | $CH_3$ | $C_4H_9(i)$ | 108–109.5 | pale yellow crystal |
| 60 | 4 | S | H | Cl | $C_2H_5$ | $C_2H_5$ | 141–143 | pale brown crystal |
| 61 | 4 | S | Cl | Cl | $C_2H_5$ | " | 88–90 | white crystal |
| 62 | 4 | S | F | Cl | " | " | 129–130.5 | " |
| 63 | 4 | S | H | Cl | $C_3H_7(i)$ | $CH_3$ | 100–102 | pale brown crystal |
| 64 | 4 | S | F | Br | $C_3H_7(i)$ | $CH_3$ | amorphous | dark yellow |
| 65 | 4 | S | H | Cl | $C_3H_7(n)$ | $C_2H_5$ | 132–134 | pale brown crystal |
| 66 | 4 | S | H | Cl | $C_3H_7(i)$ | " | 124–126 | pale yellow crystal |
| 67 | 4 | S | H | Br | $C_3H_7(i)$ | " | 121–123 | " |
| 68 | 4 | S | F | Br | $C_3H_7(i)$ | " | $n_D^{25}1.5514$ | brown oil |
| 69 | 4 | S | H | Cl | $C_3H_7(i)$ | $C_4H_9(i)$ | 123–124 | white crystal |
| 70 | 4 | S | H | Br | $C_3H_7(i)$ | " | 124–126 | pale yellow crystal |
| 71 | 4 | S | F | Br | $C_3H_7(i)$ | " | $n_D^{25}1.5421$ | brown oil |
| 72 | 4 | S | F | Cl | " | " | $n_D^{25}1.5448$ | yellow oil |
| 73 | 4 | S | H | Br | $C_4H_9(sec)$ | $CH_3$ | 80–82 | white crystal |
| 74 | 4 | S | H | Cl | " | $C_2H_5$ | 101–103 | " |
| 75 | 4 | S | H | Br | " | " | 100–101.5 | pale yellow crystal |
| 76 | 4 | S | F | Cl | " | $C_4H_9(i)$ | $n_D^{25}1.5450$ | pale brown oil |
| 77 | 5 | O | F | Cl | $C_2H_5$ | $C_2H_5$ | 81–83 | pale brown crystal |
| 78 | 5 | O | H | Br | $C_3H_7(i)$ | " | 119–122 | white crystal |
| 79 | 5 | O | Cl | Cl | " | " | 68–71 | " |
| 80 | 5 | O | F | Cl | " | " | 80–81 | " |
| 81 | 5 | S | F | Cl | $C_2H_5$ | " | amorphous | pale brown |
| 82 | 5 | S | H | Cl | $C_3H_7(i)$ | " | 121–122.5 | white crystal |
| 83 | 5 | S | H | Br | " | " | 114.5–116 | " |
| 84 | 5 | S | Cl | Cl | $C_3H_7(i)$ | " | 108.5–110.5 | white crystal |
| 85 | 5 | S | F | Cl | " | " | amorphous | pale yellow |
| 86 | 5 | S | F | Br | " | " | 99–101 | pale brown crystal |
| 87 | 4 | S | F | Cl | CHCH₂CHCH₃<br>\|      \|<br>CH₃  CH₃ | " | $n_D^{25}1.5480$ | pale yellow oil |
| 88 | 4 | S | F | Cl | $CH_2CH_2OCH_3$ | " | $n_D^{25}1.5547$ | " |
| 89 | 4 | S | F | Cl | CH₂CH(CH₂)₃CH₃<br>\|<br>C₂H₅ | " | $n_D^{25}1.5370$ | " |
| 90 | 4 | S | F | Cl | $C_3H_7(i)$ | " | $n_D^{25}1.5500$ | " |

The compound of the formula (7) and the compound of the formula (2) were obtained as follows.

1. Synthesis of 4-chloro-2-fluoro-5-isopropoxycarbonylphenylisocyanate:

5.4 ml (0.045 mol) of trichloromethylchloroformate were added to 30 ml of ethylacetate and the solution was cooled to 0° C.

Then the mixture of 13.9 g (0.06 mol) of 4-chloro-2-fluoro-5-isopropoxycarbonylaniline and 25 ml of ethylacetate were added dropwise to the above solution over the period of 15 min. and the whole was stirred for 1 hr. at 0°–10° C., thereafter heated under reflux for 2 hrs. After concentrating the reaction mixture, 15.45 g of white crystals were obtained. Yield: 99.9%, M.p.: 41°–43° C.

2. Synthesis of 2,4-dichloro-5-ethoxycarbonylphenylisothiocyanate 2.34 g (0.1 mol) of 2,4-dichloro-5-ethoxycarbonylaniline were dissolved in 80 ml of chloroform and after the solution was cooled to below 10° C., 14.9 g (0.13 mol) of thiophosgene were added to the solution dropwise and after stirred for 2 hrs. at room temperature, the whole was heated under reflux for 3 hrs., followed by concentration to obtain 27 g of pale brown crystals.

Yield: 97.7%, M.p.: 45°–46° C.

The herbicidal composition of the present invention can be used either alone or in the form of a formulation according to the purpose of its use. To promote or secure the effect, it is mixed with adjuvants to make formulations such as dust, micro granule, granule, wettable powder, flowable suspension concentrates and emulsion by means of usual procedures. These formulations are used, at the time of practical application, in the form as they are or diluted with water to desired concentration.

Those adjuvants mentioned above include carriers (diluents), extending agents, emulsifiers, wetting agents, dispersing agents, fixing agents and disintegrators.

As liquid carriers there can be used water, aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc. As solid carriers are used clay, kaolin, talc, diatomaceous earth, silica, calcium carbonate, montmorillonite, bentonite, feldspar, quartz, alumina, sawdust, etc.

As emulsifiers or dispersing agents surfactants are generally used. They include anionic, cationic, nonionic and amphoteric surfactants such as sodium salts of sulfated higher alcohol, steariltrimethylammonium chloride, polyoxyethylenealkylphenylether and lauryl betaine. Wetting agents include sodium alkylnaphthalene sulfonate and ammonium polyoxyethylenealkylphenylether sulfate, fixing agents include polyvinyl alcohol, polyvinyl acetate and CMC, and disintegrators include sodium lignin sulfonate.

Any type of said formulations can not only used alone, but also may be mixed with fungicides, insecticides, plant growth regulators, acaricides, soil modifying agents or nematocides and further can be used in combination with fertilizers or other herbicides.

The content of a compound (active ingredient) of the present invention in the formulations varies with types of formulation, methods of application and other conditions, but generally it is 0.5 to 95 weight %, preferably 2 to 50 weight %, while the content of adjuvants is 5 to 99.5 weight %, preferably 50 to 98 weight %, though sometimes the compound can be used alone.

To be more precise, a preferable range of the content is shown as under.

|  | Compound (weight %) | Adjuvant (weight %) |
| --- | --- | --- |
| Dust | 0.5–10 | 90–99.5 |
| Emulsion | 20–80 | 20–80 |
| Wettable powder | 20–80 | 20–80 |
| Granule and micro granule | 0.5–20 | 80–99.5 |
| Flowable suspension concentrate | 20–80 | 20–80 |

The formulations of the present invention can be directly applied to weeds or locus thereof.

A quantity to use of the formulations is different with kinds of the active ingredient and places of application, but generally it is within the range of 1 to 100 g, preferably 3 to 75 g, of the compound per are.

Detailed explanation will be made below on examples of formulations of the present invention and there the word "part" means part by weight.

FORMULATION EXAMPLE 1

Emulsion 35 parts of a mixture (1:1) of xylene and methylnaphthalene are added to 50 parts of Compound No. 2 to dissolve and the solution is further mixed with 15 parts of a mixture (8:2) of polyoxyethylenealkylphenylether and calcium alkylbenzenesulfonate to obtain an emulsion. It is diluted with water to use in a concentration of 0.01 to 1%.

FORMULATION EXAMPLE 2

Dust 5 parts of Compound No. 24 are mixed with 95 parts of clay and pulverized to obtain a dust. It is directly used for dusting.

FORMULATION EXAMPLE 3

Wettable powder 50 parts of Compound No. 25 are mixed with 10 parts of diatomaceous earth and 32 parts of kaolin and further uniformly blended with 8 parts of a mixture of sodium laurylsulfate and sodium 2,2'-dinaphthylmethanesulfonate, and finely pulverized to obtain a wettable powder. It is used in the form of a suspension by diluting to a concentration of 0.06 to 1%.

FORMULATION EXAMPLE 4

Granule 5 parts of a fine dust of Compound No. 24 are extended for coating on 94.5 parts of grains (16 to 32 mesh) of silica to obtain a granule, by using a methanol solution of 0.5 parts of polyvinyl polyacetate as the binding agent in a proper mixer. The granule is scattered directly in up-land field and a paddy field.

FORMULATION EXAMPLE 5

Flowable suspension concentrates 40 parts of a fine powder of Compound 24, 10 parts of ethyleneglycolmonobutylether, 10 parts of a surfactant (mixture of trioxyalkylether, polyoxyethylenenonylphenylether and sodium alkylarylsulfonate), 3 parts of colloidal aluminium silicate hydrate and 22 parts of water are uniformly mixed and further blended under stirring in a homomixer for 20 minutes to obtain a flowable. It is diluted with water for use in a concentration of 0.02 to 1%.

The excellent herbicidal activity of a compound of the present invention will be illustrated in the following test examples.

Each test was carried out on 2-replication system and the test results are given in the average value. Test Example 1: Pre-emergence treatment in flooded condition A fixed amount of paddy field soil was filled in each Wagner pot sized 1/5,000 are to provide a condition similar to a paddy field and there was sown a fixed amount of seeds of barnyard grass, monochoria, toothcup, false pimpernal, water wort and umbrella plant.

In addition tubers of arrowhead were buried 1 cm under the surface of soil at the rate of 3 pieces per pot and the pot was flooded with water 3 cm deep. Then the pot was applied with a diluted solution of the compound of the present invention at a rate of 6.25 to 25 g of the compound of the present invention per are.

Thirty days after the treatment the herbicidal activity was observed. The test results were classified on the following basis as shown in Table 3.

TABLE 3

Herbicidal activity index:
5 Complete weeding
4 up to 80% weeding
3 up to 60% weeding
2 up to 40% weeding
1 up to 20% weeding
0 no effect Test Example 1: Pre-emergence treatment under flooded condition

| Compound No. | Dosage g/a | Barnyard grass | Broadleaf (1) | Umbrella-sedge (2) | Arrowhead |
|---|---|---|---|---|---|
| 1 | 25 | 5 | 5 | 5 | 5 |
|  | 12.5 | 5 | 5 | 5 | 5 |
|  | 6.25 | 5 | 5 | 5 | 5 |
| 2 | 25 | 5 | 5 | 5 | 5 |
|  | 12.5 | 5 | 5 | 5 | 5 |
|  | 6.25 | 5 | 5 | 5 | 5 |
| 4 | 25 | 5 | 5 | 5 | 5 |
|  | 12.5 | 5 | 5 | 5 | 5 |
|  | 6.25 | 5 | 5 | 5 | 5 |
| 6 | 25 | 5 | 5 | 5 | 5 |
|  | 12.5 | 5 | 5 | 5 | 5 |
|  | 6.25 | 5 | 5 | 5 | 5 |
| 12 | 25 | 5 | 5 | 5 | 5 |
|  | 12.5 | 5 | 5 | 5 | 5 |
|  | 6.25 | 5 | 5 | 5 | 5 |
| 18 | 25 | 5 | 5 | 5 | 5 |
|  | 12.5 | 5 | 5 | 5 | 5 |
|  | 6.25 | 5 | 5 | 5 | 5 |
| 23 | 25 | 5 | 5 | 5 | 5 |
|  | 12.5 | 5 | 5 | 5 | 5 |
|  | 6.25 | 5 | 5 | 5 | 5 |
| 24 | 25 | 5 | 5 | 5 | 5 |
|  | 12.5 | 5 | 5 | 5 | 5 |
|  | 6.25 | 5 | 5 | 5 | 5 |
| 26 | 25 | 5 | 5 | 5 | 5 |
|  | 12.5 | 5 | 5 | 5 | 5 |
|  | 6.25 | 5 | 5 | 5 | 5 |
| 28 | 25 | 5 | 5 | 5 | 5 |
|  | 12.5 | 5 | 5 | 5 | 5 |
|  | 6.25 | 5 | 5 | 5 | 5 |
| 30 | 25 | 5 | 5 | 5 | 5 |
|  | 12.5 | 5 | 5 | 5 | 5 |
|  | 6.25 | 5 | 5 | 5 | 5 |
| 35 | 25 | 5 | 5 | 5 | 5 |
|  | 12.5 | 5 | 5 | 5 | 5 |
|  | 6.25 | 5 | 5 | 5 | 5 |
| 40 | 25 | 5 | 5 | 5 | 4 |
|  | 12.5 | 4 | 5 | 5 | 3 |
|  | 6.25 | 3 | 5 | 5 | 2 |
| 41 | 25 | 5 | 5 | 5 | 3 |
|  | 12.5 | 5 | 5 | 5 | 2.5 |
|  | 6.25 | 3 | 5 | 5 | 2 |
| 42 | 25 | 5 | 5 | 5 | 5 |
|  | 12.5 | 5 | 5 | 5 | 5 |
|  | 6.25 | 4.5 | 5 | 5 | 5 |
| 43 | 25 | 5 | 5 | 5 | 5 |
|  | 12.5 | 5 | 5 | 5 | 5 |
|  | 6.25 | 5 | 5 | 5 | 5 |
| 44 | 25 | 5 | 5 | 5 | 5 |
|  | 12.5 | 5 | 5 | 5 | 5 |
|  | 6.25 | 5 | 5 | 5 | 5 |
| 45 | 25 | 5 | 5 | 5 | 5 |
|  | 12.5 | 5 | 5 | 5 | 5 |
|  | 6.25 | 5 | 5 | 5 | 5 |
| 47 | 25 | 5 | 5 | 5 | 5 |
|  | 12.5 | 5 | 5 | 5 | 5 |
|  | 6.25 | 5 | 5 | 5 | 5 |
| 48 | 25 | 5 | 5 | 5 | 4 |
|  | 12.5 | 5 | 5 | 5 | 3 |
|  | 6.25 | 2 | 5 | 5 | 2 |
| 50 | 25 | 5 | 5 | 5 | 5 |
|  | 12.5 | 5 | 5 | 5 | 5 |
|  | 6.25 | 5 | 5 | 5 | 5 |
| 51 | 25 | 5 | 5 | 5 | 5 |
|  | 12.5 | 5 | 5 | 5 | 5 |
|  | 6.25 | 5 | 5 | 5 | 5 |
| 52 | 25 | 5 | 5 | 5 | 5 |
|  | 12.5 | 3 | 5 | 5 | 3 |
|  | 6.25 | 2 | 5 | 5 | 2 |
| 54 | 25 | 5 | 5 | 5 | 5 |
|  | 12.5 | 5 | 5 | 5 | 5 |
|  | 6.25 | 5 | 5 | 5 | 5 |
| 56 | 25 | 5 | 5 | 5 | 5 |
|  | 12.5 | 5 | 5 | 5 | 4 |
|  | 6.25 | 3 | 5 | 5 | 3 |
| 57 | 25 | 5 | 5 | 5 | 5 |
|  | 12.5 | 5 | 5 | 5 | 5 |
|  | 6.25 | 5 | 5 | 5 | 5 |
| 59 | 25 | 5 | 5 | 5 | 5 |
|  | 12.5 | 5 | 5 | 5 | 5 |
|  | 6.25 | 3 | 5 | 5 | 5 |
| 60 | 25 | 5 | 5 | 5 | 5 |
|  | 12.5 | 5 | 5 | 5 | 5 |
|  | 6.25 | 5 | 5 | 5 | 5 |
| 61 | 25 | 5 | 5 | 5 | 5 |
|  | 12.5 | 5 | 5 | 5 | 5 |
|  | 6.25 | 5 | 5 | 5 | 5 |
| 62 | 25 | 5 | 5 | 5 | 5 |
|  | 12.5 | 5 | 5 | 5 | 5 |
|  | 6.25 | 5 | 5 | 5 | 5 |
| 63 | 25 | 5 | 5 | 5 | 5 |
|  | 12.5 | 5 | 5 | 5 | 5 |
|  | 6.25 | 5 | 5 | 5 | 5 |
| 64 | 25 | 5 | 5 | 5 | 5 |
|  | 12.5 | 5 | 5 | 5 | 5 |
|  | 6.25 | 5 | 5 | 5 | 5 |
| 66 | 25 | 5 | 5 | 5 | 5 |
|  | 12.5 | 5 | 5 | 5 | 5 |
|  | 6.25 | 5 | 5 | 5 | 5 |
| 68 | 25 | 5 | 5 | 5 | 5 |
|  | 12.5 | 5 | 5 | 5 | 5 |
|  | 6.25 | 5 | 5 | 5 | 5 |
| 71 | 25 | 5 | 5 | 5 | 5 |
|  | 12.5 | 5 | 5 | 5 | 5 |
|  | 6.25 | 5 | 5 | 5 | 5 |
| 72 | 25 | 5 | 5 | 5 | 5 |
|  | 12.5 | 5 | 5 | 5 | 5 |
|  | 6.25 | 5 | 5 | 5 | 5 |
| 74 | 25 | 5 | 5 | 5 | 5 |
|  | 12.5 | 5 | 5 | 5 | 5 |
|  | 6.25 | 5 | 5 | 5 | 5 |
| 75 | 25 | 5 | 5 | 5 | 5 |
|  | 12.5 | 5 | 5 | 5 | 5 |
|  | 6.25 | 5 | 5 | 5 | 5 |
| 76 | 25 | 5 | 5 | 5 | 5 |
|  | 12.5 | 5 | 5 | 5 | 5 |
|  | 6.25 | 5 | 5 | 5 | 5 |
| 81 | 25 | 5 | 5 | 5 | 5 |
|  | 12.5 | 5 | 5 | 5 | 5 |
|  | 6.25 | 5 | 5 | 5 | 5 |

TABLE 3-continued

| | | | | | |
|---|---|---|---|---|---|
| 82 | 25 | 5 | 5 | 5 | 5 |
| | 12.5 | 5 | 5 | 5 | 5 |
| | 6.25 | 5 | 5 | 5 | 5 |
| 83 | 25 | 5 | 5 | 5 | 5 |
| | 12.5 | 5 | 5 | 5 | 5 |
| | 6.25 | 5 | 5 | 5 | 5 |
| 85 | 25 | 5 | 5 | 5 | 5 |
| | 12.5 | 5 | 5 | 5 | 5 |
| | 6.25 | 5 | 5 | 5 | 5 |
| 86 | 25 | 5 | 5 | 5 | 5 |
| | 12.5 | 5 | 5 | 5 | 5 |
| | 6.25 | 5 | 5 | 5 | 5 |
| 88 | 25 | 5 | 5 | 5 | 5 |
| | 12.5 | 5 | 5 | 5 | 5 |
| | 6.25 | 5 | 5 | 5 | 5 |
| Control A | 25 | 3 | 4 | 3 | 0 |
| | 12.5 | 1 | 2 | 0 | 0 |

Remarks
(1) Broadleaf: mixture of barnyard grass, toothcup, false pimpernel, water wort
(2) Umbrella-sedge: Umbrella plant
Control A

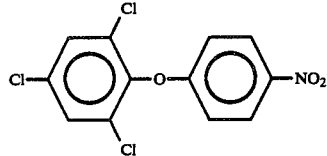

TEST EXAMPLE 2

Post-emergence treatment in flooded condition

A fixed amount of paddy field soil was filled in each Wagner pot sized 1/5,000 are to provide a condition similar to a paddy field and there was sown a fixed amount of seeds of barnyard grass, monochoria, toothcup, false pimpernel, water wort and umbrella plant.

In addition tubers of arrowhead were buried 1 cm under the surface of soil at the rate of 3 pieces per pot, three 2.5-leaf stage rice seedlings (variety: Nihonbare) were transplanted from a nursery, the pot was flooded with water 3 cm deep and then placed in a greenhouse.

When the seeds grew to reach 2 to 3-leaf stage, a diluted solution of the compound of the present invention, was applied to the flood at a rate of 6.25, 12.5, 50 g of the compound of the present invention per are.

After 30 days from the treatment with the diluted solution, the phytotoxicity against paddy rice and the herbicidal activity were observed and obtained the results as shown in Table 4. The classification basis of the herbicidal activity is the same with Test Example 1, and that of the phytotoxicity is as follows:

TABLE 4

Test Example 2: Post-emergemce treatmemt under flooded condition

| Compound No. | Dosage g/a | Herbicidal activity | | | | Phytotoxicity against paddy rice |
|---|---|---|---|---|---|---|
| | | Barnyard grass | Broad leaf(1) | Umbrella sedge(2) | Arrow-head | |
| 3 | 25 | 5 | 5 | 5 | 5 | — |
| | 12.5 | 4 | 5 | 5 | 5 | — |
| 10 | 25 | 5 | 5 | 5 | 5 | — |
| | 12.5 | 5 | 5 | 5 | 5 | — |
| 11 | 25 | 5 | 5 | 5 | 5 | + |
| | 12.5 | 5 | 5 | 5 | 5 | — |
| 14 | 25 | 5 | 5 | 5 | 5 | + |
| | 12.5 | 4.5 | 5 | 5 | 5 | ± |
| 15 | 25 | 5 | 5 | 5 | 5 | + |
| | 12.5 | 5 | 5 | 5 | 5 | ± |
| 19 | 25 | 5 | 5 | 5 | 5 | — |
| | 12.5 | 5 | 5 | 5 | 5 | — |
| 22 | 25 | 5 | 5 | 5 | 5 | — |
| | 12.5 | 4 | 5 | 5 | 5 | — |
| 27 | 25 | 5 | 5 | 5 | 5 | ± |
| | 12.5 | 5 | 5 | 5 | 5 | — |
| 29 | 25 | 5 | 5 | 5 | 5 | — |
| | 12.5 | 5 | 5 | 5 | 5 | — |
| 31 | 50 | 5 | 5 | 5 | 5 | + |
| | 25 | 5 | 5 | 5 | 5 | ± |
| 33 | 50 | 5 | 5 | 5 | 5 | + |
| | 25 | 5 | 5 | 5 | 5 | ± |
| 34 | 25 | 5 | 5 | 5 | 5 | ++ |
| | 12.5 | 5 | 5 | 5 | 5 | + |
| 35 | 25 | 5 | 5 | 5 | 5 | ++ |
| | 12.5 | 5 | 5 | 5 | 5 | + |
| 39 | 25 | 3 | 5 | 5 | 3 | — |
| | 12.5 | 2.5 | 5 | 5 | 2 | — |
| | 6.25 | 2 | 5 | 5 | 2 | — |
| 45 | 25 | 5 | 5 | 5 | 4.5 | — |
| | 12.5 | 5 | 5 | 5 | 4 | — |
| | 6.25 | 2 | 5 | 5 | 3 | — |
| 46 | 25 | 5 | 5 | 5 | 5 | — |
| | 12.5 | 5 | 5 | 5 | 5 | — |
| | 6.25 | 5 | 5 | 5 | 4.5 | — |
| 47 | 25 | 5 | 5 | 5 | 5 | ++ |
| | 12.5 | 5 | 5 | 5 | 5 | + |
| | 6.25 | 5 | 5 | 5 | 5 | — |
| 49 | 25 | 3 | 5 | 5 | 3.5 | — |
| | 12.5 | 2 | 5 | 5 | 3 | — |
| | 6.25 | 2 | 5 | 5 | 2 | — |
| 51 | 25 | 5 | 5 | 5 | 5 | — |
| | 12.5 | 4.5 | 5 | 5 | 4 | — |
| | 6.25 | 4 | 5 | 5 | 3 | — |
| 52 | 25 | 5 | 5 | 5 | 4 | — |
| | 12.5 | 4 | 5 | 5 | 3 | — |
| | 6.25 | 3 | 5 | 5 | 2 | — |
| 54 | 25 | 5 | 5 | 5 | 5 | — |
| | 12.5 | 5 | 5 | 5 | 5 | — |
| | 6.25 | 3 | 5 | 5 | 4 | — |
| 57 | 25 | 5 | 5 | 5 | 5 | + |
| | 12.5 | 5 | 5 | 5 | 5 | ± |
| | 6.25 | 4.5 | 5 | 5 | 5 | — |
| 59 | 25 | 5 | 5 | 5 | 5 | ++ |
| | 12.5 | 5 | 5 | 5 | 5 | + |
| | 6.25 | 5 | 5 | 5 | 5 | + |
| 60 | 25 | 5 | 5 | 5 | 5 | + |
| | 12.5 | 5 | 5 | 5 | 5 | + |
| | 6.25 | 5 | 5 | 5 | 5 | ± |
| 65 | 25 | 5 | 5 | 5 | 5 | ++ |
| | 12.5 | 5 | 5 | 5 | 5 | ± |
| | 6.25 | 5 | 5 | 5 | 5 | ± |
| 67 | 25 | 5 | 5 | 5 | 5 | + |
| | 12.5 | 5 | 5 | 5 | 5 | ± |
| | 6.25 | 5 | 5 | 5 | 5 | ± |
| 69 | 25 | 5 | 5 | 5 | 5 | + |
| | 12.5 | 5 | 5 | 5 | 5 | ± |
| | 6.25 | 5 | 5 | 5 | 5 | — |
| 70 | 25 | 5 | 5 | 5 | 5 | + |
| | 12.5 | 5 | 5 | 5 | 5 | + |
| | 6.25 | 5 | 5 | 5 | 5 | ± |
| 73 | 25 | 5 | 5 | 5 | 5 | ± |
| | 12.5 | 5 | 5 | 5 | 5 | — |
| | 6.25 | 4.5 | 5 | 5 | 5 | — |
| 74 | 25 | 5 | 5 | 5 | 5 | + |
| | 12.5 | 5 | 5 | 5 | 5 | ± |
| | 6.25 | 5 | 5 | 5 | 5 | — |
| 75 | 25 | 5 | 5 | 5 | 5 | ++ |
| | 12.5 | 5 | 5 | 5 | 5 | + |
| | 6.25 | 5 | 5 | 5 | 5 | — |
| 77 | 25 | 5 | 5 | 5 | 5 | — |
| | 12.5 | 2 | 4 | 4 | 3 | — |
| | 6.25 | 2 | 4 | 4 | 2 | — |
| 81 | 25 | 5 | 5 | 5 | 5 | ++ |
| | 12.5 | 5 | 5 | 5 | 5 | ++ |
| | 6.25 | 5 | 5 | 5 | 5 | — |

TABLE 4-continued

Test Example 2: Post-emergemce treatmemt under flooded condition

| Compound No. | Dosage g/a | Herbicidal activity | | | | Phytotoxicity against paddy rice |
|---|---|---|---|---|---|---|
| | | Barnyard grass | Broad leaf(1) | Umbrella sedge(2) | Arrowhead | |
| 82 | 25 | 5 | 5 | 5 | 5 | ++ |
| | 12.5 | 5 | 5 | 5 | 5 | + |
| | 6.25 | 5 | 5 | 5 | 5 | — |
| 83 | 25 | 5 | 5 | 5 | 5 | + |
| | 12.5 | 5 | 5 | 5 | 5 | + |
| | 6.25 | 5 | 5 | 5 | 5 | — |
| Control A | 25 | 0 | 0 | 0 | 0 | — |
| | 12.5 | 0 | 0 | 0 | 0 | — |
| | 6.25 | 0 | 0 | 0 | 0 | — |

— no damage
+ slight damage
++ some damage
+++ moderate damage
++++ heavy damage
x complete death As seen in the results of Test examples 1 and 2, the compounds of the present invention showed remarkable herbicidal effect against the principal annual and perennial weeds in paddy fields in pre- and post emergence treatment.

Furthermore, it was found that the compound of the present invention showed only little phytotoxicity in pre- and post transplantation treatment.

Then the Test examples in field are shown as follows.

TEST EXAMPLE 3

Pre-emergence soil surface treatment

A fixed amount of field soil was filled in a round plastic case 8 cm across and 8 cm deep, and a fixed amount of seeds of crabgrass, foxtail, pigweed, buckwheat was sown followed by covering them with soil 0.5 to 1 cm thick. Then immediately a diluted solution of the compound of the present invention was applied to treat the whole surface of soil in case at a rate of 12.5 to 25 g of the compound of the present invention per are.

After the treatment the cultivation was done in a greenhouse and the herbicidal activity was observed on the 20th day. The test was carried out on 2-replication system and each average value was sought. The judging standard of the results is the same with Test Example 1. The test results are shown in Table 5.

TABLE 5

Test Example 3: Pre-emergence soil surface treatment

| Compound No. | Dosage g/a | Herbicidal Effect | | | |
|---|---|---|---|---|---|
| | | Foxtail | Crabgrass | Pigweed | Buckwheat |
| 1 | 25 | 5 | 5 | 5 | 5 |
| | 12.5 | 5 | 5 | 5 | 5 |
| 2 | 25 | 5 | 5 | 5 | 5 |
| | 12.5 | 4.5 | 4.5 | 5 | 5 |
| 5 | 25 | 5 | 5 | 5 | 5 |
| | 12.5 | 5 | 5 | 5 | 5 |
| 8 | 25 | 5 | 5 | 5 | 5 |
| | 12.5 | 5 | 5 | 5 | 5 |
| 11 | 25 | 5 | 5 | 5 | 5 |
| | 12.5 | 5 | 5 | 5 | 5 |
| 12 | 25 | 5 | 5 | 5 | 5 |
| | 12.5 | 5 | 5 | 5 | 5 |
| 13 | 25 | 5 | 5 | 5 | 5 |
| | 12.5 | 5 | 5 | 5 | 5 |
| 24 | 25 | 5 | 5 | 5 | 5 |
| | 12.5 | 5 | 5 | 5 | 5 |
| 26 | 25 | 5 | 5 | 5 | 5 |
| | 12.5 | 5 | 5 | 5 | 5 |

TABLE 5-continued

Test Example 3: Pre-emergence soil surface treatment

| Compound No. | Dosage g/a | Herbicidal Effect | | | |
|---|---|---|---|---|---|
| | | Foxtail | Crabgrass | Pigweed | Buckwheat |
| 30 | 25 | 5 | 5 | 5 | 5 |
| | 12.5 | 5 | 4.5 | 5 | 5 |
| 34 | 25 | 5 | 5 | 5 | 5 |
| | 12.5 | 5 | 5 | 5 | 5 |
| 42 | 25 | 4 | 4.5 | 5 | 5 |
| | 12.5 | 3 | 3 | 5 | 5 |
| 43 | 25 | 4.5 | 5 | 5 | 5 |
| | 12.5 | 3 | 3 | 5 | 5 |
| 44 | 25 | 4.5 | 5 | 5 | 5 |
| | 12.5 | 3 | 4 | 5 | 5 |
| 60 | 25 | 5 | 5 | 5 | 5 |
| | 12.5 | 4 | 3 | 5 | 5 |
| 62 | 25 | 5 | 5 | 5 | 5 |
| | 12.5 | 5 | 5 | 5 | 5 |
| 63 | 25 | 4 | 4.5 | 5 | 5 |
| | 12.5 | 3 | 4 | 5 | 5 |
| 64 | 25 | 5 | 5 | 5 | 5 |
| | 12.5 | 5 | 5 | 5 | 5 |
| 68 | 25 | 5 | 5 | 5 | 5 |
| | 12.5 | 5 | 5 | 5 | 5 |
| 71 | 25 | 5 | 5 | 5 | 5 |
| | 12.5 | 4 | 5 | 5 | 5 |
| 72 | 25 | 4 | 5 | 5 | 5 |
| | 12.5 | 3 | 5 | 5 | 5 |
| 75 | 25 | 4 | 4 | 5 | 5 |
| | 12.5 | 3 | 3 | 5 | 5 |
| 81 | 25 | 4 | 5 | 5 | 5 |
| | 12.5 | 3 | 4.5 | 5 | 5 |
| 86 | 25 | 4 | 5 | 5 | 5 |
| | 12.5 | 3 | 4 | 5 | 5 |
| Control A | 25 | 0 | 0 | 0 | 0 |
| | 12.5 | 0 | 0 | 0 | 0 |
| Control B | 25 | 4 | 4.5 | 5 | 5 |
| | 12.5 | 2 | 3 | 5 | 5 |

Control B

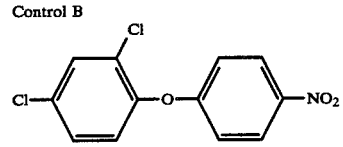

TEST EXAMPLE 4

Post-emergence treatment

A fixed amount of field soil was filled in a round plastic case 8 cm across and 8 cm deep, and a fixed amount of seeds of foxtail (or crabgrass), pigweed was sown. When they grew up to 3 to 4-leaf stage, a wettable powder containing the compound of the present invention was sprayed on the body of plants after diluting it at a rate of 12.5, 25 or 50 g of active ingredient per are.

The test was conducted on 2-replication system. Twenty days after the treatment the test results were observed on the same judging standard and the results are shown in Table 6.

TABLE 6

Test Example 4: Post-emergence treatment

| Compound No. | Dosage g/a | Herbicidal effect | |
|---|---|---|---|
| | | foxtail | pigweed |
| 1 | 50 | 5 | 5 |
| | 25 | 5 | 5 |
| | 12.5 | 4 | 5 |
| 2 | 50 | 5 | 5 |
| | 25 | 5 | 5 |
| | 12.5 | 4.5 | 5 |
| 5 | 50 | 5 | 5 |
| | 25 | 5 | 5 |

TABLE 6-continued

Test Example 4: Post-emergence treatment

| Compound No. | Dosage g/a | Herbicidal effect crabgrass | pigweed |
|---|---|---|---|
| 7 | 12.5 | 5 | 5 |
|   | 50 | 5 | 5 |
|   | 25 | 5 | 5 |
| 11 | 12.5 | 4 | 5 |
|   | 50 | 5 | 5 |
|   | 25 | 5 | 5 |
| 12 | 12.5 | 3 | 5 |
|   | 50 | 5 | 5 |
|   | 25 | 5 | 5 |
| 13 | 12.5 | 5 | 5 |
|   | 50 | 5 | 5 |
|   | 25 | 5 | 5 |
| 16 | 12.5 | 5 | 5 |
|   | 50 | 5 | 5 |
|   | 25 | 4 | 5 |
| 20 | 12.5 | 3.5 | 5 |
|   | 50 | 5 | 5 |
|   | 25 | 4 | 5 |
| 23 | 12.5 | 3 | 5 |
|   | 50 | 5 | 5 |
|   | 25 | 4.5 | 5 |
| 24 | 12.5 | 3.5 | 5 |
|   | 50 | 5 | 5 |
|   | 25 | 5 | 5 |
| 26 | 12.5 | 5 | 5 |
|   | 50 | 5 | 5 |
|   | 25 | 5 | 5 |
| 30 | 12.5 | 5 | 5 |
|   | 50 | 5 | 5 |
|   | 25 | 4.5 | 5 |
| 33 | 12.5 | 3.5 | 5 |
|   | 50 | 4 | 5 |
|   | 25 | 2.5 | 4.5 |
| 35 | 12.5 | 2 | 4 |
|   | 50 | 5 | 5 |
|   | 25 | 5 | 5 |
|   | 12.5 | 5 | 5 |
| Control B | 50 | 5 | 5 |
|   | 25 | 3 | 5 |
|   | 12.5 | 2 | 4.5 |
| 41 | 50 | 5 | 5 |
|   | 25 | 4 | 5 |
|   | 12.5 | 3 | 5 |
| 45 | 50 | 4 | 5 |
|   | 25 | 3 | 5 |
|   | 12.5 | 2 | 5 |
| 47 | 50 | 5 | 5 |
|   | 25 | 4 | 5 |
|   | 12.5 | 3 | 5 |
| 50 | 50 | 4 | 5 |
|   | 25 | 3 | 5 |
|   | 12.5 | 2 | 5 |
| 57 | 50 | 5 | 5 |
|   | 25 | 3 | 5 |
|   | 12.5 | 2.5 | 5 |
| 59 | 50 | 5 | 5 |
|   | 25 | 3.5 | 5 |
|   | 12.5 | 2.5 | 5 |
| 61 | 50 | 5 | 5 |
|   | 25 | 3 | 5 |
|   | 12.5 | 2 | 5 |
| 65 | 50 | 5 | 5 |
|   | 25 | 3 | 5 |
|   | 12.5 | 2 | 5 |
| 68 | 50 | 5 | 5 |
|   | 25 | 3 | 5 |
|   | 12.5 | 2 | 5 |
| 71 | 50 | 5 | 5 |
|   | 25 | 3 | 5 |
|   | 12.5 | 2 | 5 |
| 72 | 50 | 5 | 5 |
|   | 25 | 4 | 5 |
|   | 12.5 | 3 | 5 |
| 74 | 50 | 5 | 5 |
|   | 25 | 3 | 5 |
|   | 12.5 | 2 | 5 |
| 76 | 50 | 5 | 5 |
| 82 | 25 | 3 | 5 |
|   | 12.5 | 2 | 5 |
|   | 50 | 5 | 5 |
|   | 25 | 4 | 5 |
|   | 12.5 | 3 | 5 |
| 84 | 50 | 5 | 5 |
|   | 25 | 3 | 5 |
|   | 12.5 | 2 | 5 |
| 85 | 50 | 5 | 5 |
|   | 25 | 3 | 5 |
|   | 12.5 | 2 | 5 |
| Control A | 50 | 0 | 0 |
|   | 25 | 0 | 0 |
|   | 12.5 | 0 | 0 |

TEST EXAMPLE 5

Phytotoxicity against crops

A fixed amount of field soil was filled in a plastic vessel sized 23 cm×4.5 cm×12.5 cm and a fixed amount of seeds of soybean, cotton, corn, wheat, sunflower and rice was sown followed by 3-cm thick covering with soil.

Then immediately a diluted solution of the compound of the present invention was sprayed on the soil surface with a small sprayer at the rate of 25 to 50 g of the compound of the present invention.

After the treatment the crops were grown in a greenhouse and 20 days later the degree of phytotoxicity against each crop was observed. The test was carried out on 2-replication system and each average value was sought.

The judging standard of test results is the same with Test Example 2 and the results are shown in Table 7.

TABLE 7

Test Example: Phytotoxicity

| Compound No. | Dosage g/a | Phytotoxicity against crops |  |  |  |  |  |
|---|---|---|---|---|---|---|---|
|  |  | Soy bean | Cotton | Corn | Wheat | Rice | Sun flower |
| 1 | 50 | — | ± | — | — | — | — |
|   | 25 | — | — | — | — | — | — |
| 2 | 50 | — | ± | — | — | — | — |
|   | 25 | — | — | — | — | — | — |
| 5 | 50 | — | — | — | — | — | — |
|   | 25 | — | — | — | — | — | — |
| 8 | 50 | — | — | — | — | — | — |
|   | 25 | — | — | — | — | — | — |
| 11 | 50 | — | ± | — | — | — | — |
|   | 25 | — | — | — | — | — | — |
| 12 | 50 | — | — | — | — | — | — |
|   | 25 | — | — | — | — | — | — |
| 25 | 50 | — | ± | — | — | — | — |
|   | 25 | — | — | — | — | — | — |
| 30 | 50 | — | — | — | — | — | — |
|   | 25 | — | — | — | — | — | — |
| Control B | 50 | +++ | ++ | ++ | +++ | + | +++ |
|   | 25 | + | + | + | + | — | ++ |
| 43 | 50 | — | — | — | — | — | — |
|   | 25 | — | — | — | — | — | — |
| 60 | 50 | — | — | — | — | — | — |
|   | 25 | — | — | — | — | — | — |
| 62 | 50 | — | — | — | — | — | — |
|   | 25 | — | — | — | — | — | — |
| 64 | 50 | — | — | — | — | — | — |
|   | 25 | — | — | — | — | — | — |
| 68 | 50 | — | — | — | — | — | — |
|   | 25 | — | — | — | — | — | — |
| 71 | 50 | — | — | — | — | — | — |
|   | 25 | — | — | — | — | — | — |
| 72 | 50 | — | — | — | — | — | — |
|   | 25 | — | — | — | — | — | — |
| 72 | 50 | — | — | — | — | — | — |
|   | 25 | — | — | — | — | — | — |

TABLE 7-continued

| | | Test Example: Phytotoxicity | | | | | |
|---|---|---|---|---|---|---|---|
| Com- | | Phytotoxicity against crops | | | | | |
| pound No. | Dosage g/a | Soy bean | Cotton | Corn | Wheat | Rice | Sun flower |
| 81 | 50 | — | — | — | — | — | — |
| | 25 | — | — | — | — | — | — |
| Control A | 50 | — | — | — | — | — | — |
| | 25 | — | — | — | — | — | — |

As obvious from the results of Test Examples 4 and 5, the compound of the present invention proves to show very good herbicidal activity both in pre-emergence and post-emergence treatments of main weeds in the field. On the other hand, it is clear from the results of Test Example 5 that the compound of the present invention has no phytotoxicity against crops and is a suitable herbicide for use in farmlands.

What we claim is:

1. A compound selected from the group consisting of

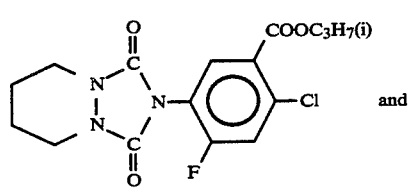 and

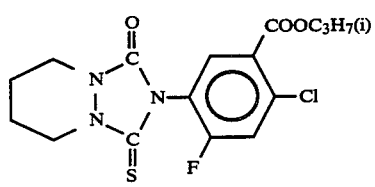

2. A herbicidal composition which comprises 0.5 to 95% by weight of a compound selected from the group consisting of

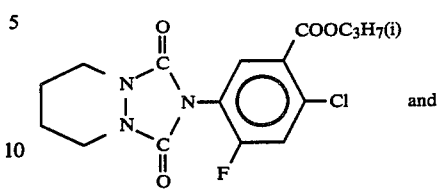 and

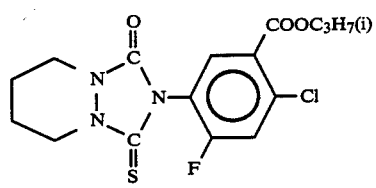

as an effective component and 5 to 99.5% by weight of adjuvant(s).

3. A method for killing weed which comprises applying to weeds or the lows thereof a herbicidally effective amount of a compound selected from the group consisting of

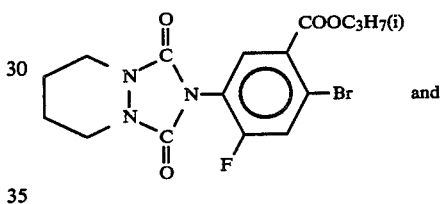 and

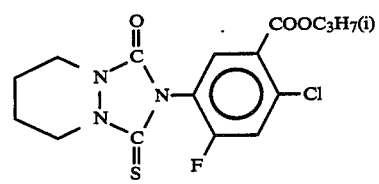

* * * * *